United States Patent [19]

Huth et al.

[11] Patent Number: 5,102,936

[45] Date of Patent: Apr. 7, 1992

[54] COPOLYMERS BASED ON ETHYLENICALLY UNSATURATED MONOMERS AND CONTAINING URETHANE GROUPS, PROCESSES FOR THEIR PREPARATION AND THEIR USE

[75] Inventors: Hans-Ullrich Huth, Egelsbach; Klaus Zimmerschied, Wiesbaden, both of Fed. Rep. of Germany

[73] Assignee: Hoechst AG, Fed. Rep. of Germany

[21] Appl. No.: 600,513

[22] Filed: Oct. 19, 1990

[30] Foreign Application Priority Data

Oct. 21, 1989 [DE] Fed. Rep. of Germany ....... 3935137

[51] Int. Cl.$^5$ .............................................. C08L 43/02
[52] U.S. Cl. .................................... 524/247; 524/248; 524/555; 526/240; 526/301; 526/287; 526/278
[58] Field of Search ............... 526/301, 240, 278, 287; 524/813, 555, 547, 548; 525/328.2, 328.4

[56] References Cited

U.S. PATENT DOCUMENTS

| Re. 33,008 | 8/1989  | Ruffner | 526/270 |
|------------|---------|---------|---------|
| Re. 33,156 | 1/1990  | Shay    | 526/301 |
| 4,514,522  | 4/1985  | Shay    | 526/301 |
| 4,600,761  | 7/1986  | Ruffner | 526/270 |
| 4,703,080  | 10/1987 | Shay    | 524/555 |
| 4,722,962  | 2/1988  | Shay    | 524/548 |
| 4,801,671  | 1/1989  | Shay    | 526/214 |
| 4,916,183  | 4/1990  | Barron  | 524/555 |

*Primary Examiner*—Joseph L. Schofer
*Assistant Examiner*—M. Nagumo
*Attorney, Agent, or Firm*—Bierman and Muserlian

[57] ABSTRACT

Copolymers based on ethylenically unsaturated monomers and containing urethane groups, processes for their preparation and their use.

Copolymers prepared by free-radical-initiated copolymerization of ethylenically unsaturated copolymerizable monomers, in which the copolymers are preferably synthesized from a) 25 to 85% by weight of ethylenically unsaturated hydrophobic monomers, and b) 1 to 50% by weight of ethylenically unsaturated monomers capable of salt formation, and c) 0.1 to 30% by weight of surface-active urethane derivatives containing ethylenically unsaturated carboxyl or carbamido radicals, and d) 0 to 10% by weight of other ethylenically unsaturated monomers different from a) to c) and containing functional radicals, and e) 0 to 5% by weight of ethylenically unsaturated carbonyl compounds, and f) 0 to 5% by weight of ethylenically polyunsaturated or polyfunctional monomers capable of crosslinking, and g) 0 to 5% by weight of molecular weight regulators, and, if aqueous dispersions or the copolymers isolated therefrom are present, these furthermore contain h) 0.1 to 10% by weight, relative to the total amount of all monomer units in the copolymer, of emulsifiers and/or protective colloids, and, if desired, the copolymers are partially or completely neutralized and converted into water-soluble or colloid-water-dispersible copolymer salts and, if desired, are obtained in solid form.

Use of the products as viscosity-increasing and rheology-modifying thickener substances in aqueous systems.

9 Claims, No Drawings

COPOLYMERS BASED ON ETHYLENICALLY UNSATURATED MONOMERS AND CONTAINING URETHANE GROUPS, PROCESSES FOR THEIR PREPARATION AND THEIR USE

DESCRIPTION

The invention relates to copolymers based on ethylenically unsaturated monomers, which contain monomer units comprising surface-active urethane derivatives having ethylenically unsaturated carboxyl or carbamido radicals, ethylenically unsaturated monomers having anionic or cationic radicals capable of salt formation, ethylenically unsaturated hydrophobic monomers and, if desired, further ethylenically unsaturated monomers other than the monomers already mentioned, to processes for the preparation thereof, in particular by free radical-initiated emulsion, suspension, bead or solution copolymerization and to their use as thickener components which have an advantageous rheology-modifying effect in aqueous systems, preferably in aqueous polymer dispersions, paints, plasters and fillers and/or aqueous binder systems containing pigments.

The preparation of ethylenically unsaturated surface-active monomers containing urethane groups and their use as so-called macromonomers for the copolymerization and preparation of alkali-soluble thickener dispersion copolymers is already known from EP-OS-197,635. The preparation of these macromonomers containing urethane groups is carried out by reaction of polyalkylene glycol aryl or alkyl ethers at their terminal OH group with ethylenically unsaturated isocyanates, such as, for example isocyanatoethyl (meth)acrylate. In the copolymers prepared therefrom, the polyalkylene glycol aryl or alkyl ether radical is bound to the main chain of the copolymer molecule as side chain of the macromonomer unit via a urethane bond. However, the thickener products described have previously not been able to achieve practical importance, since in particular their rheology-modifying properties have proven unsatisfactory.

In European Patent 84,227, liquid mixtures containing acryloyl and alkylacryloyl poly(alkoxycarbamates) and their use for radiation-curable coatings are disclosed. The publication does not contain any mention or indication of their usability for the preparation of copolymers or of thickener copolymers.

European Patent 121,230 has disclosed copolymers containing monomer units with surface-active crotonic esters and unsaturated carboxylic acids, which can be used as rheologically active thickeners in aqueous systems. The copolymers can contain specifically, for example, 1 to 45% by weight of (meth)acrylic acid, 30 to 85% by weight of (meth)acrylic esters of (C -C :)-alcohols and 0.5 to 30% by weight of surface-active crotonic esters of polyethoxylated, long-chain alcohols or alkylphenols. The products are water-soluble in the alkaline pH region and have a high thickener effect. They can be used, for example, in aqueous gloss emulsion paints for modifying the rheology. The coating properties of gloss paints thickened in this manner, such as, for example, flow and spreading resistance of the paint, efficiency at low binder concentration or efficiency in a mixture with pigments and/or fillers and water stability and gloss of the dried coating can, however, fulfil the requirements in practice only insufficiently. Thus, although the thickeners described in European Patent 121,230 and mentioned above have a high thickener capacity and are capable of keeping the viscosity of an aqueous emulsion paint stable at a sufficiently high value at a high shear rate in accordance with the spreading resistance desired in practice when the paint is applied by means of a brush, the resulting rheology-modifying effects are, however, insufficient when applying the emulsion paint by means of a roller especially on vertical walls and on ceilings. The reason for this is that the thickeners mentioned, which contain macromonomeric surface-active crotonic ester monomer units have a low-shear viscosity which is too low, so that paints containing these products tend to spatter. On the other hand, comparable thickeners containing no macromonomeric surface-active crotonic ester monomer units in the carboxyl-containing copolymers lack the spreading resistance, i.e. their high-shear viscosity is too low.

Accordingly, the object of the invention was to provide a copolymer influencing the rheology of aqueous systems and having a thickening effect in aqueous preparations, which even at the lowest possible concentration has a high thickener capacity and produces or imparts sufficient, preferably very high, viscosities which are stable over fairly large concentration ranges in aqueous systems, such as, for example, in gel- or paste-like industrial products, emulsion paints, synthetic plasters, emulsion tile adhesives not only in the low but also the high shear region and can be used in particular as effective thickener for the preparation of non-spattering paints.

It has now been possible surprisingly to achieve the object formulated above by using specific copolymers based on ethylenically unsaturated monomers which contain macromonomer units of surface-active urethane derivatives with ethylenically unsaturated carboxyl and carbamido radicals and units of ethylenically unsaturated monomers capable of salt formation and have been prepared by free radical-initiated copolymerization using conventional methods. A particularly preferred copolymerization method is emulsion copolymerization.

The majority of the surface-active macromonomer urethane derivatives with ethylenically unsaturated carboxyl or carbamido radicals used as comonomers according to the invention, such as are defined below by the formula I, are the subject-matter of Patent Application HOE 89/F 342 (File No. P. 3,935,138.6) submitted on the same day, to which reference is made.

Pendant urethane bonds in the copolymers according to the invention are, owing to the structure of the comonomeric ethylenically unsaturated, surface-active macromonomer urethane derivatives of the formula I, not located on the main-chain beginning of the side chains but mainly at the end of the side chains, which leads to a surprisingly advantageous property profile in the copolymers, in particular with respect to their thickener effect.

According to the invention, particularly preferably those monomeric ethylenically unsaturated surface-active macromonomer urethane derivatives of the formula I according to the invention are used for the copolymerization which in their monomeric form at 20° C. are solid, wax-like or paste-like.

The invention therefore relates to copolymers based on ethylenically unsaturated monomers containing monomer units of surface-active urethane derivatives with ethylenically unsaturated carboxyl or carbamido radicals and units of ethylenically unsaturated, monomers capable of salt formation and having been prepared by free-radical-initiated solution, emulsion, suspension or bead copolymerization or to the solutions or aqueous dispersions thereof or the salts thereof or solutions or dispersions of the salts, wherein the copolymer particles, relative to the total amount of monomer units in the copolymer in % by weight, have preferably been synthesized from (a) 25 to 85% by weight of ethylenically unsaturated hydrophobic monomers from the group comprising vinyl esters of $(C_1-C_{18})$-monocarboxylic acids, preferably vinyl acetate, vinyl propionate, vinyl versatate, vinyl laurate, vinyl stearate, (meth)acrylic esters of $(C_1-C_{22})$-alcohols, preferably methyl methacrylate, butyl methacrylate, octyl methacrylate, ethyl acrylate, isobutyl acrylate, 2-ethylhexylacrylate, vinyl aromatics having up to 18 carbon atoms, preferably styrene and vinyltoluene, vinyl chloride, ethylene, (meth)acrylonitrile, diesters of maleic acid and/or fumaric acid with $(C_1-C_{22})$-alcohols, vinylpyrrolidone, and (b) 1 to 50% by weight of ethylenically unsaturated monomers capable of salt formation and containing functional anionic radicals from the group comprising —COOH, sulfonic acids or sulfonic acid derivatives or phosphonic acids or phosphonic acid derivatives, preferably carboxyl radicals, in particular monomers from the group comprising ethylenically 15 unsaturated $(C_3-C_5)$-mono- or dicarboxylic acids, such as acrylic acid, methacrylic acid, crotonic acid, itaconic acid, maleic acid, fumaric acid and monoesters of dibasic carboxylic acids with straight-chain or branched $(C_3-C_5)$-alcohols, furthermore monomers from the group comprising vinylsulfonic acids, (3-sulfopropyl)-methacrylic esters, acrylamidomethylpropanesulfonic acid, vinylphosphonic acid, acrylamidomethylpropanephosphonic acid or salts thereof, preferably alkali metal salts or ammonium salts, or instead of anionic monomers, ethylenically unsaturated monomers capable of salt formation and containing functional cationic radicals from the group comprising —$NR^5R^6$, where $R^5$ and $R^6$ can be identical or different and be H or $(C_1-C_{18})$-alkyl, or $R^5$ and $R^6$ together with N can, if desired, form a five- to seven-membered heterocyclic ring, preferably dimethylaminoneopentyl (meth)acrylate, dimethylaminopropyl(meth)acrylamide, dimethyl-aminoethyl (meth)acrylate, 2-N-morpholinoethyl (meth)acrylate, tertbutylaminoethyl (meth)acrylate, ethylenically unsaturated $(C_3-C_{18})$-aliphatic primary amines or secondary amines containing a $(C_1-C_{18})$-alkyl radical or tertiary amines containing two $(C_1-C_{18})$-alkyl radicals, and (c) 0.1 to 30% by weight of ethylenically unsaturated surface-active urethane derivatives of the formula I,

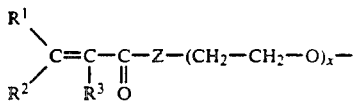
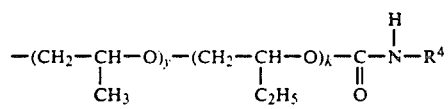

in which the radicals $R^1$ to $R^4$ and Z and the numbered indices x, y and k have the following meanings:

$R^1$, $R^2$, $R^3$, which can be identical or different, are H, —$CH_3$, —COOH, —$CH_2$—COOH, preferably H, —$CH_3$, Z is oxygen or NH, preferably oxygen, x, y, k, which can be identical or different, are 0 to 100, with the proviso that $x+y+k \geqq 2$, preferably $x+y = 2$ to 30, if k is 0, $R^4$ is substituted or unsubstituted $(C_1-C_{30})$-alkyl, preferably $(C_6-C_{10})$-alkyl, substituted or unsubstituted $(C_7-C_{30})$-aryl, substituted or unsubstituted $(C_7-C_{30})$-aralkyl, substituted or unsubstituted $(C_5-C_8)$-cycloalkyl, substituted or unsubstituted 5- to 7-membered heterocycle, particularly preferred urethane derivatives being those in which, in the formula I, $R^1$, $R^2$ are H, $R^3$ is —$CH_3$ or $R^1$, $R^3$ are H, $R^2$ is —$CH_3$, Z is oxygen and x+y is 2 to 30, if k is 0, and (d) 0 to 10% by weight of further ethylenically unsaturated monomers different from (a) to (c) and having functional radicals from the group comprising

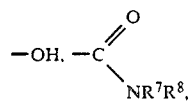

where $R^7$ and $R^8$ can be identical or different and are H, $(C_1-C_6)$-alkyl, $(C_2-C_8)$-alkoxyalkyl, $(C_5-C_7)$-cycloalkyl or $(C_6-C_{18})$-aralkyl, or $R^7$ and $R^8$ toether with N form, if desired, a five- to seven-membered heterocyclic ring, preferably ethylenically unsaturated hydroxyalkyl esters of (meth)acrylic acid, in particular hydroxyethyl-(meth)acrylate, hydroxypropyl (meth)acrylate, polyalkyleneoxide esters of (meth)acrylic acid, in particular containing 2 to 50 ethylene oxide units and/or 2 to 50 propylene oxide units, in which the terminal OH groups of the ester or polyalkylene glycol ether radicals can also be etherified or esterified, ethylenically unsaturated amides, in particular (meth)acrylamide, N-methylacrylamide, N,N-dimethyl(meth)acrylamide, N-butylmethacrylamide, N-cyclohexylmethacrylamide, N-benzylmethacrylamide, N-methylol(meth)acrylamide,N-butoxymethyl(meth)acrylamide, and (e) 0 to 5% by weight of ethylenically unsaturated carbonyl compounds, preferably from the group comprising vinyl methyl ketone, acrolein, crotonaldehyde, allyl acetoacetate, acetoacetoxyethyl (meth)acrylate, and (f) 0 to 5% by weight of ethylenically polyunsaturated or polyfunctional monomers capable of crosslinking, preferably from the group comprising divinylbenzene, diallyl phthalate, butanediol diacrylate, triethylene glycol dimethacrylate, allyl methacrylate, bisphenol A diethylene glycol dimethacrylate, triallyl cyanurate, methylene-bis(meth)acrylamide, and (g) 0 to 5% by weight of molecular weight regulators from the group comprising dodecylmercaptan, carbon tetrachloride, α-methylstyrene, toluene, bromotrichloromethane, tetrakis(mercaptoacetyl)pentaerythritol, thioglycolic acid, and when aqueous dispersions or the copolymers isolated therefrom are present, they furthermore contain (h) 0.1 to 10% by weight, relative to the total amount of all monomer units in the copolymer, of emulsifiers and/or if desired, protective colloids, preferably from the group comprising anionic or cationic or zwitter ionic and/or in particular nonionic surfactants and/or protective colloids.

The preparation of the ethylenically unsaturated, surface-active urethane derivatives of the formula I

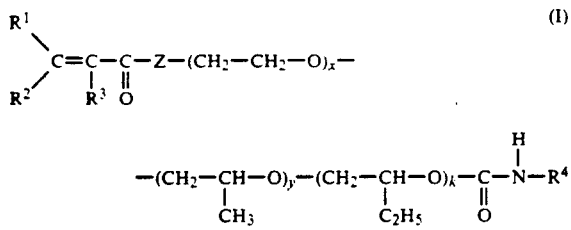

in which $R^1$ to $R^4$, Z, x, y and k have the abovementioned meaning, and which are used according to the invention as comonomers for the copolymerization and have been described above under the comonomer unit group (c) is carried out by reacting isocyanates with hydroxypolyoxyalkyleneoxycarbonylalkenes or with N-(hydroxypolyoxyalkylene)-alkenecarboxamides by reacting isocyanates of the formula II

in which $R^4$ has the meaning as in formula I, with equimolar amounts of hydroxy compounds of the formula III

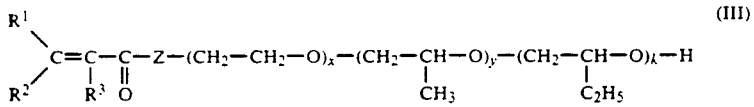

in which $R^1$, $R^2$, $R^3$, Z, x, y and k have the meanings as in formula I.

Preferred compounds of the formula III are polyalkylene glycol monoesters of ethylenically unsaturated carboxylic acids, preferably of acrylic acid, methacrylic acid or crotonic acid.

The reaction of the components of the formulae II and III is preferably carried out in the absence of a solvent or in inert organic solvents or, if appropriate, in other copolymerizable ethylenically unsaturated monomers (so-called reactive diluents) used for the copolymerization according to the invention and being inert under the reaction conditions in the absence of water, preferably at temperatures between 0° C. and room temperature, or at elevated temperature, preferably up to 60° C.

Suitable inert organic solvents are the inert solvents usually used in organic syntheses with isocyanates in anhydrous medium, as long as they can fulfil, inter alia, the requirements with respect to dissolving effect and boiling range.

Examples of preferred inert solvents are toluene, tetrahydrofuran (THF), ethyl acetate and hexane.

In some cases it may be advantageous to use reactive diluents as solvents. Reactive diluents are copolymerizable monomers which are inert under the synthesis conditions of urethane group formation, but can later be copolymerized under suitable polymerization conditions with the unsaturated urethane derivatives of the formula I. Accordingly, preferred inert reactive diluents are those which can be used as additional comonomers for the copolymerization according to the invention, such as, for example, (meth)acrylic esters, styrene and vinyl esters, it being preferred to remain under the saturation concentration of the reactants when they are used.

During the isocyanate addition reaction, the concomitant use of a catalyst may be desirable, so that, inter alia, the reaction temperature can be kept very low, which may be advantageous especially if reactive diluents are used. Preferred catalysts are organic tin compounds, which are preferably dissolved in an inert organic solvent.

The use of dibutyltin dilaurate, if appropriate in combination with tert-butylcatechol, is particularly preferred.

If the copolymers according to the invention are partially or completely neutralized or their radicals capable of salt formation are partially or completely converted into the salt form, they become increasingly to completely water-soluble or colloid-water-soluble or colloid-water-dispersible in water. In such a partially or completely neutralized form, they can act or be used as thickeners of aqueous systems, showing surprisingly advantageous rheology-modifying properties in the sense described above.

Accordingly, the invention further relates to the copolymers according to the invention described above in their partially or completely neutralized water-soluble or colloid-water-dispersible form, the neutralization of the anionic copolymers having been effected with bases and that of the cationic copolymers with acids. The partial or complete neutralization of the copolymers according to the invention is preferably carried out in their aqueous dispersion form. In some cases, it may also be advantageous to carry out the neutralization reaction in solutions of their copolymers in organic solvents.

A preferred neutralization method furthermore consists, inter alia, in mixing, for example, the anionic, unneutralized copolymers in their water-insoluble acid form as solutions in a suitable organic solvent or in particular as low-viscosity aqueous dispersion with the thickening aqueous or water-containing system and then neutralizing the resulting mixture partially or completely by adding a base, which converts the copolymers, which exhibit a thickening effect and rheology-modifying effect, into a water-soluble salt form. In an analogous manner, the cationic, unneutralized copolymers when used in their water-insoluble basic form can be converted by reaction with acids into water-soluble salt forms, in which they can develop the thickening effect according to the invention and the rheology-modifying effect.

As already described above, the copolymers according to the invention can be prepared, for example, by a conventional, free-radical-initiated solution copolymerization in customary organic solvents, or preferably in the form of an aqueous copolymer dispersion by a conventional free-radical-initiated emulsion copolymerization. In these, the solids content of aqueous copolymer dispersions prepared in this manner is preferably in the range of 10 to 55% by weight of solid, relative to the dispersion.

In the preferred emulsion copolymerization, the monomer, surface-active urethane derivatives of the formula I mentioned above as comonomer components (c) are furthermore initially introduced preferably into the water phase.

When the copolymers according to the invention are prepared by free-radical-initiated solution copolymerization, preferably in conventional organic solvents and by customary methods, the resulting copolymers are preferably isolated or obtained in finely dispersed powder or granule form and, if desired, freed from volatile components by subsequent drying.

When the copolymers according to the invention are prepared by emulsion copolymerization, it is likewise possible to use customary methods. It is possible to use customary ionic and/or nonionic emulsifiers for emulsifying the monomers and stabilizing the resulting latices. Examples of preferred anionic emulsifiers in the preparation of anionic emulsion copolymers are surface-active alkyl sulfates, alkylsulfonates, alkylaryl sulfates, alkylarylsulfonates, alkali metal salts and/or ammonium salts of alkyl- or alkylarylglycol ether sulfates.

Examples of preferred nonionic emulsifiers are surface-active ethoxylated fatty alcohols or ethoxylated alkylphenols.

Examples of preferred emulsifiers in the preparation of cationic emulsion polymers are nonionic emulsifiers and/or cationic surfactants, preferably from the group comprising ethoxylated fatty amines, quaternary alkylammonium compounds and salts of fatty amines.

Accordingly, the invention further relates to processes for the preparation of the copolymers according to the invention described above by free-radical-initiated emulsions or solution copolymerization of the ethylenically unsaturated copolymerizable monomers mentioned in the required mixing ratios by methods known per se and, if desired, subsequent partial or complete neutralization of the monomer units capable of salt formation with the formation of copolymer salts which are colloid-dispersible in water or water-soluble, the neutralization of anionic copolymers being effected by addition of bases or basic compounds and the neutralization of cationic copolymers by addition of acids or acid compounds.

A particularly preferred procedure is emulsion copolymerization, in which again preferably the ethylenically-unsaturated surface-active urethane derivatives of the formula I described above as comonomer component c) are initially introduced into the aqueous phase. The copolymer proportion of the aqueous copolymer dispersions according to the invention prepared in such a manner by emulsion copolymerization is preferably 10 to 55% by weight, in particular 25 to 50% by weight.

In the case of emulsion copolymerization, it may furthermore be of crucial importance whether the monomers are added or metered in for the copolymerization reaction as such or in aqueous emulsion form. The type of addition of the emulsifier also has a similar important effect. Thus, depending on whether the emulsifier is initially introduced into the aqueous phase or is metered in during the copolymerization, large differences with respect to particle size of the copolymers, to particle size distribution and to the stability of the copolymer dispersions can result.

The relative amounts of the comonomer components a) to f) and of the further components g) and h) described above can be varied in all copolymerization processes according to the invention within a relatively broad range, and are relative to the total amount of all comonomers a) to f) in % by weight, in each case preferably for (a) 25 to 85% by weight, in particular 40 to 80, particularly preferably 50 to 75, % by weight, for (b) 1 to 50% by weight, in particular 5 to 45, particularly preferably 8 to 40, % by weight, for (c) 0.1 to 30% by weight, in particular 1 to 25, particularly preferably 3 to 20, % by weight, for (d) 0 to 10% by weight, in particular 0.1 to 8, particularly preferably 1 to 6, % by weight, for (e) 0 to 5% by weight, in particulr 0.05 to 3, particularly preferably 0.1 to 2% by weight, and for (f) 0 to 5% by weight, in particular 0.01 to 1%, particularly preferably 0.1 to 0.5, % by weight.

(Components (g) and (h) are used, relative to the total amount of all comonomers (a) to (f) in % by weight, in each case preferably in amounts of for (g) 0 to 5% by weight, in particular 0.05 to 3, particularly preferably 0.1 to 2, % by weight and, in emulsion copolymerization (h) 0.1 to 10% by weight, in particular 0.1 to 6, particularly preferably 0.2 to 3, % by weight.

To initiate the emulsion copolymerization, customary water-soluble initiators which start free radical chains are preferably used in amounts of 0.01 to 2% by weight, relative to the total amount of all comonomers.

Examples of particularly suitable initiators for this are alkali metal persulfate or ammonium persulfate, $H_2O_2$, tert-butyl hydroperoxide, customary redox catalysts, 4,4,-azobis(4-cyanovaleric acid), 2,2,-azobis(N,N,-dimethyleneisobutyraaidine) dihydrochloride, 2,2,-azobis(2-amidinopropane) dihydrochloride, the two last-mentioned initiators being suitable in particular for the preparation of cationic copolymers, furthermore high-energy radiation and customary photoinitiators.

To increase the thickener capacity or to further influence the rheological properties and efficiency of dissolved copolymers according to the invention in aqueous systems, it may be advantageous in some cases to use additional ethylenically polyunsaturated monomers, preferably from the monomer component group (f), described above, as comonomers in the copolymerization, in order to achieve higher molecular weights in the copolymers. For example, diallyl phthalate, divinylbenzene, allyl methacrylate or ethylene glycol dimethacrylate are preferably used as such crosslinking comonomers leading to increases in the molecular weight. The amounts used can preferably be in the range between 0 and 5% by weight, relative to the entire amount of comonomers, and can be in particular 0.01 to 1% by weight, particularly preferably 0.1 to 0.5% by weight. The ethylenically polyunsaturated comonomers can form molecule branching and networks during the copolymerization, which, after partial or complete neutralization of the copolymer, can lead to the formation of gel structures and thus to the formation of specific rheological property profiles in aqueous systems which are advantageous for some applications. The concomitant use of molecular weight regulators from the component group g) described above during the copolymerization makes it possible to reduce the molecular weights of the copolymers. However, with decreasing molecular weights of the copolymers, the thickening effect of neutralized copolymers in aqueous systems diminishes, and the viscosities of comparable aqueous solutions of partially or completely neutralized copolymers decrease with decreasing molecular weights, compared with copolymers prepared in the absence of molecular weight regulators. However, by means of the molecular weight regulators, it is possible to improve the possibilities to harmonize the equilibrium between the viscosity of the neutralized copolymers in aqueous systems at high and low shear stress and adapt it in a controlled manner for specific applications. Although the molecular weights of copolymers according to the invention are not subject to a specific limit, especially an upper limit, they are however in the lower region, preferably above 10,000 g/mol, in particular above 30,000 g/mol.

In principle, all compounds which have free-radical-transferring properties are suitable as molecular weight regulator in the copolymerization. The compounds described above under the component group g) are preferably used for this. Monofunctional or polyfunctional mercaptans, such as, for example, dodecylmercaptan, tetrakis(mercaptoacetyl)pentaerythritol, and thioglycolic acid are particularly preferably used.

Furthermore, preferred examples are also α-methylstyrene, toluene, bromotrichloromethane and carbon tetrachloride. The amount of regulator used can be preferably in the range between 0 and 5% by weight, relative to the entire amount of comonomers, and can be in particular 0.05 to 3% by weight, particularly preferably 0.1 to 2% by weight. The copolymers according to the invention have surprisingly high thickener capacities in their partially and/or completely neutralized form in aqueous systems. It is particularly advantageous and surprising that they exhibit high viscosities in aqueous medium not only in the low but also in the high shear region, which makes them suitable, inter alia, in particular for the preparation of non-spattering paints. A further important advantage is that the copolymers according to the invention are hydrolytically stable not only in the acid but also in the alkaline pH range. The advantageous spectrum of properties of the copolymers according to the invention allows their use as thickeners in smaller amounts than in the comparable use of comparable copolymers, which admittedly also contain methacrylic acid and acrylic ester units but no monomer units of surface-active urethane derivatives of the formula I, as described above under the component group c), in order to give aqueous systems certain rheological properties. The high specific thickener effect of the products according to the invention, which is effective over a broad application range, makes it possible to achieve the necessary effects even with relatively small amounts used in the formulations to be thickened, so that virtually no deleterious effects on other properties in the ready-to-use formulations, such as, for example, water-sensitivity of paints prepared therefrom and dried, can occur, in contrast to conventional thickeners, which for formulations of comparable rheology have to be used in significantly higher amounts, which can in general frequently lead to the known troublesome and damaging water sensitivities in the final products, for example in the dried paints.

The effectiveness of the copolymers according to the invention as thickener for aqueous systems preferably results from their partially or completely neutralized form, the neutralization in anionic copolymers being effected by addition of inorganic or organic bases and in cationic copolymers by addition of organic or inorganic acids, in each case in accordance with the stoichiometry. The neutralization converts the copolymers according to the invention which, in their unneutralized form, are in general water-insoluble into a water-soluble or a colloid-water-soluble or water-dispersible form, in which they develop their thickener effect in aqueous systems and can impart to these systems specific and stable rheological properties. In anionic copolymers, the alkali metal salts, ammonium salts and amine salts or, if partially neutralized, the corresponding partial salts are particularly preferred.

In cationic copolymers, the salts of mineral acids and mono- or polycarboxylic acids are particularly preferred.

Furthermore, the anionic copolymers or the partially neutralized and fully neutralized water-soluble salt forms thereof, including their use as thickeners and rheology-modifying components in aqueous systems, are particularly preferred.

The copolymers according to the invention are preferably and particularly advantageously used as thickeners for aqueous systems in such a manner that they are mixed in their unneutralized form as low-viscosity copolymer solution in a suitable solvent or as low-viscosity aqueous copolymer dispersion with the aqueous system to be thickened, and the resulting mixture, including any additionally used auxiliaries, additives, pigments, paint components, etc., which must be stable at the pH values to be established, is then partially or completely neutralized in anionic thickeners by addition of bases and in cationic thickeners by addition of acids and, if desired, brought to a slightly alkaline pH in the case of anionic thickeners or to a slightly acidic pH in the case of cationic thickeners. The preferred pH range of the neutralization using bases is 5 to 10.5, preferably 8 to 9.5, and of the neutralization using acids 2 to 6.5, preferably 3 to 5.5.

The unneutralized copolymers are particuarly preferably mixed with the aqueous systems to be thickened in the form of aqueous copolymer dispersions.

The preferred area of application for the copolymers according to the invention is their use as thickener for thickening and adjusting the viscosity of aqueous solutions and of disperse aqueous systems, preferably, for example, of aqueous emulsion paints, gloss emulsion paints, textile printing pastes, paper printing pastes, solutions and dispersions of biocides, in particular for plant protection and for combating pests, liquid fertilizers, emulsion cleaners, pickling pastes, de-icing agents and cosmetic preparations.

A further interesting application of the copolymers according to the invention is their use as sizing materials in the textile industry or as sizing material components which can be easily washed out by alkaline or acid liquors.

In aqueous emulsion paints and in aqueous gloss emulsion paints, the use of the copolymers according to the invention is, for example, particularly advantageous for achieving the rheological properties desired by the user, such as high high-shear viscosity and high low-shear viscosity, the latter property being of importance for non-spattering paint formulations. High high-shear viscosity is understood to mean values, determined on, for example, 5% strength by weight aqueous thickener solutions, of between 0.01 and 1 Pa.s at a shear rate of D 10,000. $s^{-1}$, and high low-shear viscosity is understood to mean values of between 0.1 and 100 Pa.s at D=0.1. $s^{-1}$.

The amounts of the copolymers according to the invention used are not critical. However, when used as thickeners, they are preferably in the range of 0.01 to 5% by weight of copolymer, relative to the aqueous system to be thickened.

The invention is illustrated in more detail by the examples which follow:

EXAMPLE 1

Preparation of an emulsion copolymer having the comonomer formula I-urethane compound

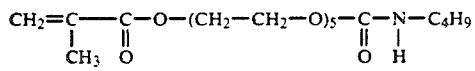

In a (2 l) three-neck flask equipped with stirrer, reflux condenser and internal thermometer, 28 g of the sodium salt of an alkyl aryl polyglycol ether sulfate (50% strength by weight) are dissolved in 738 g of deionized water, and the solution is heated to 80° C. with stirring. 10 ml of an initiator solution comprising 0.25 g of ammonium persulfate in 50 g of deionized water are added as are 50 g of a monomer mixture comprising 252 g of ethyl acrylate (=72% by weight), 63 g of methacrylic acid (=18% by weight) and 35 g of the abovementioned monomer formula I-urethane compound (=10% by weight, in each case based on the entire amount of monomers). The remaining monomer mixture is then metered in, starting after half an hour, together with the remaining initiator solution over a period of two hours. After the metering in has been completed, heating is continued for another hour while continuing the stirring, and the batch is then brought to room temperature. The solids content of the resulting dispersion is adjusted to 30% by weight.

The copolymer portion can be converted into a water-soluble form having the desired properties of thickening aqueous systems and modifying the rheology by partial or complete neutralization of the dispersion using aqueous sodium hydroxide solution or aqueous ammonia. The copolymer components can be obtained in dry form, preferably in powder form or granule form, by the removal of water from the dispersion or solution by conventional methods, preferably, for example, by precipitation and/or drying. The viscosity numbers, measured in the Epprecht rheomat on the copolymer completely neutralized with sodium hydroxide solution in 5% strength by weight aqueous solution at 20° C., are $10 \times 10^{-2}$ Pa.s at D=10,000. $s^{-1}$ and $12 \times 10^{-1}$ Pa.s at D=0.1. $s^{-1}$.

EXAMPLE 2

Example 1 is repeated, except that the monomer mixture used is composed of 50% by weight of ethyl acrylate, 40% by weight of methacrylic acid, 10% by weight of the monomer formula I-urethane compound

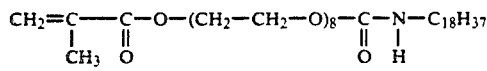

and additionally 0.1% by weight, relative to the entire amount of monomers, of the molecular weight regulator n-dodecylmercaptan. The solids content of the resulting dispersion is adjusted to 30% by weight.

The partial or complete neutralization of the copolymer portion and, if desired, its isolation in dry form can be carried out analogously to Example 1. The viscosity numbers, measured in the Epprecht rheomat on the copolymer completely neutralized with sodium hydroxide solution in 5 and 1% strength by weight aqueous solution at 20° C., are $4.2 \times 10^{-2}$ Pa.s at D=10,000. $s^{-1}$ and $610 \times 10^{-1}$ Pa.s at D=0.1. $s^{-1}$.

EXAMPLE 3

Example 1 is repeated, except that the monomer mixture used is composed of 55% by weight of ethyl acrylate, 40% by weight of methacrylic acid, 5% by weight of the monomer formula I-urethane compound

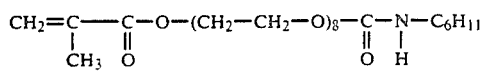

and additionally 0.1% by weight, relative to the entire amount of monomers, of n-dodecylmercaptan. The solids content of the resulting dispersion is adjusted to 30% by weight.

The partial or complete neutralization of the copolymer portion and, if desired, its isolation in dry form can be carried out analogously to Example The viscosity numbers, measured in the Epprecht rheomat on the copolymer completely neutralized with sodium hydroxide solution in 5% strength by weight aqueous solution at 20° C., are $11 \times 10^{-2}$ Pa.s at D10,000. $s^{-1}$ and $18 \times 10^{-1}$ Pa.s at D=0.1. $s^{-1}$.

EXAMPLE 4

Example 1 is repeated, except that the monomer mixture used is composed of 72% by weight of ethyl acrylate, 18% by weight of methacrylic acid, 10% by weight of the monomer formula I-urethane compound

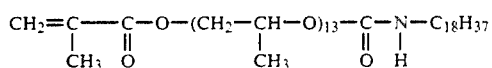

and additionally 0.1% by weight, relative to the entire amount of monomers, of n-dodecylmercaptan. The solids content of the resulting dispersion is adjusted to 30% by weight.

The partial or complete neutralization of the copolymer portion and, if desired, its isolation in dry form can be carried out analogously to Example 1. The viscosity numbers, measured in the Epprecht rheomat on the copolymer completely neutralized with sodium hydroxide solution in 5% strength by weight aqueous solution at 20° C., are $8.2 \times 10^{-2}$ Pa.s at D=10,000. $s^{-1}$ and $4.5 \times 10^{-1}$ Pa.s at D=0.1. $s^{-1}$.

EXAMPLE 5

Example 1 is repeated, except that the monomer mixture used is composed of 80% by weight of ethyl acrylate, 15% 2by weight of methacrylic acid, 5% by weight of the monomer formula I-urethane compound

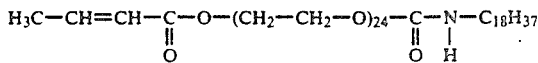

The solids content of the resulting dispersion is adjusted to 30% by weight

The partial or complete neutralization of the copolymer portion and, if desired, its isolation in dry form can be carried out analogously to Example 1. The viscosity numbers, measured in the Epprecht rheomat on the copolymer completely neutralized with sodium hydroxide solution in 1% strength by weight aqueous solution at 20° C.. are $9.1 \times 10^{-2}$ Pa.s at $D = 10,000. s^{-1}$ and $2.1 \times 10^{-1}$ Pa.s at $D = 0.1. s^{-1}$.

COMPARATIVE EXAMPLE 1

Example 1 is repeated, except that the monomer mixture used is composed of 60% by weight of ethyl acrylate, 40% by weight of methacrylic acid, and additionally 0.2% by weight, relative to the entire amount of monomers, of n-dodecylmercaptan. The solids content of the resulting dispersion is adjusted to 30% by weight.

The partial or complete neutralization of the copolymer portion and, if desired, its isolation in dry form can be carried out analogously to Example 1. The viscosity numbers, measured in the Epprecht rheomat on the copolymer completely neutralized with sodium hydroxide solution in 5% strength by weight aqueous solution at 20° C.. are $5.2 \times 10^{-2}$ Pa.s at $D = 10,000. s^{-1}$ and $6.9 \times 10^{-2}$ Pa.s at $D = 0.1. s^{-1}$.

We claim:

1. A copolymer based on ethylenically unsaturated monomers containing monomer units of surface-active urethane derivatives with ethylenically unsaturated carboxyl or carbamido radicals and units of ethylenically unsaturated monomers capable of salt formation and having been prepared by free-radical-initiated copolymerization in solution, emulsion, suspension or by bead copolymerization or solutions or aqueous dispersions thereof or the salts thereof or solutions or dispersions of the salts, wherein the copolymer particles, relative to the total amount of monomer units in the copolymer in % by weight, have been synthesized from (a) 25 to 85% by weight of ethylenically unsaturated hydrophobic monomers from the group comprising vinyl esters of $(C_1-C_{18})$-monocarboxylic acids, acrylic esters or (meth)acrylic esters of $(C_1-C_{22})$-alcohols, vinyl aromatics having up to 18 carbon atoms, vinyl chloride, ethylene, acrylonitrile or (meth)acrylonitrile, diesters of maleic acid and/or fumaric acid with $(C_1-C_{22})$-alcohols, vinylpyrrolidone, and p1 (b) 1 to 50% by weight of ethylenically unsaturated monomers capable of salt formation and containing functional anionic radicals from the group comprising —COOH, sulfonic acids or sulfonic acid derivatives or phosphonic acids or phosphonic acid derivatives, carboxylic acids from the group comprising ethylenically unsaturated $(C_3-C_5)$-mono- or dicarboxylic acids, and monoesters of dibasic carboxylic acids with straight-chain or branched $(C_1-C_8)$-alcohols, furthermore monomers from the group comprising vinylsulfonic acid, (3-sulfopropyl)methacrylic esters, acrylamidomethylpropanesulfonic acid, vinylphosphonic acid, acrylamidomethylpropanephosphonic acid or salts thereof, or instead of anionic monomers, ethylenically unsaturated monomers capable of salt formation and containing functional cationic radicals from the group comprising —$NR^5R^6$, where $R^5$ and $R^6$ can be identical or different and be H or $(C_1-C_{18})$-alkyl, or $R^5$ and $R^6$ together with N can form a five- to seven-membered heterocyclic ring, or ethylenically unsaturated $(C_3-C_{18})$-aliphatic primary amines or secondary amines containing a $(C_1-C_{18})$-alkyl radical or tertiary amines containing two $(C_1-C_{18})$-alkyl radicals, and (c) 0.1 to 30% by weight of ethylenically unsaturated surface-active urethane derivatives of the formula I,

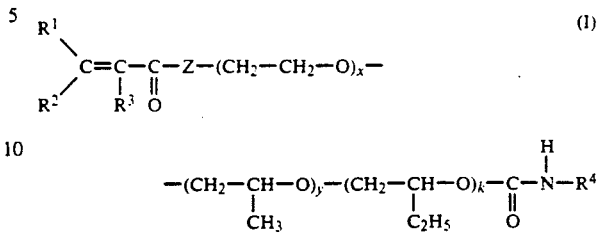

in which the radicals $R^1$ to $R^4$ and Z and the numbered indices x, y and k have the following meanings:

$R^1$, $R^2$, $R^3$, which can be identical or different, are H, —$CH_3$, —COOH, —$CH_2$—COOH, Z is oxygen or NH, x, y, k, which can be identical or different, are 0 to 100, with the proviso that $x + y + k \geq 2$, $R^4$ is $(C_1-C_{30})$-alkyl which may be substituted, $(C_8-C_{10})$-aryl which may be substituted, $(C_7-C_{30})$-aralkyl which may be substituted, $(C_5-C_8)$-cycloalkyl which may be substituted, a 5- to 7-membered heterocycle which may be substituted, and (d) 0 to 10% by weight of further ethylenically unsaturated monomers different from (a) to (c) and having functional radicals from the group comprising

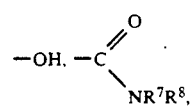

where $R^7$ and $r^8$ can be identical or different and are H, $(C_1-C_6$-alkyl), $(C_2-C_8)$-alkoxyalkyl, $(C_5-C_7)$-cycloalkyl or $(C_6-C_{18})$-aralkyl, or $R^7$ and $R^8$ together with N form a five- to seven-membered heterocyclic ring, or ethylenically unsaturated hydroxyalkyl esters or polyalkyleneoxide esters of acrylic acid or (meth)acrylic acid, in which the terminal OH groups of the ester or polyalkylene glycol ether radicals can also be etherified or esterified, ethylenically unsaturated amides, and (e) 0 to 5% by weight of ethylenically unsaturated carbonyl compounds, and (f) 0 to 5% by weight of ethylenically polyunsaturated or polyfunctional monomers capable of crosslinking, and (g) 0 to 5% by weight of molecular weight regulators from the group comprising dodecylmercaptan, carbon tetrachloride, α-methylstyrene, toluene, bromotrichloromethane, tetrakis(mercaptoacetyl)-pentaerythritol, thioglycolic acid, and when aqueous dispersions or the copolymers isolated therefrom are present, they furthermore contain (h) 0.1 to 10% by weight, relative to the total amount of all monomer units in the copolymer, emulsifiers and/or protective colloids.

2. A copolymer as claimed in claim 1, which is present in partially or completely neutralized water-soluble or colloid-water-dispersible form.

3. A process for the preparation of copolymers by free-radical-initiated emulsion or solution copolymerization of ethylenically unsaturated copolymerizable monomers, it being possible for the groups of the copolymers capable of salt formation to be subsequently partially or completely neutralized and for the copolymers to be isolated as dispersion or as solution or in dried form, which comprises copolymerizing as comonomers (a) 25 to 85% by weight of ethylenically unsaturated hydrophobic monomers from the group comprising vinyl esters of ($C_1$-$C_{18}$)-monocarboxylic acids, acrylic esters or (meth)acrylic esters of ($C_1$—$C_{22}$)-alcohols, vinyl aromatics having up to 18 carbon atoms, vinyl chloride, ethylene, acrylonitrile or (meth)acrylonitrile, diesters of maleic acid and/or fumaric acid with ($C_1$-$C_{22}$)-alcohols, vinylpyrrolidone, and (b) 1 to 50% by weight of ethylenically unsaturated monomers capable of salt formation and containing functional anionic radicals from the group comprising —COOH, sulfonic acids or sulfonic acid derivatives or phosphonic acids or phosphonic acid derivatives, carboxylic acids from the group comprising ethylenically unsaturated ($C_3$-$C_5$)-mono- or dicarboxylic acids, and monoesters of dibasic carboxylic acids with straight-chain or branched ($C_1$-$C_8$)-alcohols, furthermore monomers from the group comprising vinylsulfonic acid, (3-sulfopropyl)methacrylic esters, acrylamidomethylpropanesulfonic acid, vinylphosphonic acid, acrylamidomethylpropanephosphonic acid or salts thereof, or instead of anionic monomers, ethylenically unsaturated monomers capable of salt formation and containing functional cationic radicals from the group comprising —$NR^5R^6$, where $R^5$ and $R^6$ can be identical or different and be H or ($C_1$-$C_{18}$)-alkyl, or $R^5$ and $R^6$ together with N can form a five- to seven-membered heterocyclic ring, or ethylenically unsaturated ($C_3$-$C_{18}$)-aliphatic primary amines or secondary amines containing a ($C_1$-$C_{18}$)-alkyl radical or tertiary amines containing two ($C_1$-$C_{18}$)-alkyl radicals, and (c) 0.1 to 30% by weight of ethylenically unsaturated surface-active urethane derivatives of the formula I,

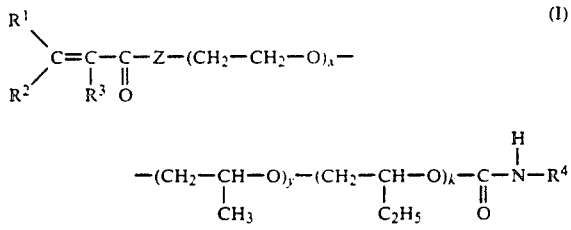

in which the radicals $R^1$ to $R^4$ and Z and the numbered indices x, y and k have the following meanings:

$R^1$, $R^2$, $R^3$, which can be identical or different, are H, —$CH_3$, —COOH, —$CH_2$—COOH, Z is oxygen or NH, x, y, k, which can be identical or different, are 0 to 100, with the proviso that $x+y+k \geq 2$, $R^4$ is $C_1$-$C_{30}$-alkyl which may be substituted, ($C_6$-$C_{10}$)-aryl which may be substituted, ($C_{hd} 7$-$C_{30}$)-aralkyl which may be substituted, ($C_5$-$C_8$)-cycloalkyl which may be substituted, 5- to 7-membered heterocycle which may be substituted, and (d) 0 to 10% by weight of further ethylenically unsaturated monomers different from (a) to (c) and having functional radicals from the group comprising

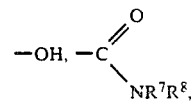

where $R^7$ and $R^8$ can be identical or different and are H, ($C_1$-$C_6$-alkyl, ($C_2$-$C_8$)-alkoxyalkyl, ($C_5$-$C_7$)-cycloalkyl or ($C_6$-$C_{18}$)-aralkyl, or $R^7$ and $R^8$ together with N form a five- to seven-membered heterocyclic ring, or ethylenically unsaturated hydroxyalkyl esters or polyalkyleneoxide esters of acrylic acid or (meth)acrylic acid, in which the terminal OH groups of the ester or polyalkylene glycol ether radicals can also be etherified or esterified, ethylenically unsaturated amides, and (e) 0 to 5% by weight of ethylenically unsaturated carbonyl compounds, and (f) 0 to 5% by weight of ethylenically polyunsaturated or polyfunctional monomers capable of crosslinking, and (g) 0 to 5% by weight of molecular weight regulators from the group comprising dodecylmercaptan, carbon tetrachloride, α-methylstyrene, toluene, bromotrichloromethane, tetrakis(mercaptoacetyl)-pentaerythritol, thioglycolic acid, and furthermore in the case of emulsion copolymerization adding (h) 0.1 to 10% by weight, relative to the total amount of all monomer units in the copolymer, of emulsifiers and/or if desired, protective colloids, obtaining the resulting copolymer as a dispersion, as a solution or in solid form, or converting it by partial or complete neutralization, by addition of bases in the case of anionic copolymers and by addition of acids in the case of cationic copolymers into a water-soluble or colloid-water-dispersible copolymer salt and obtaining the copolymer product as a solution or dispersion or in solid form by eliminating the solvent or dispersant in a conventional manner.

4. The process as claimed in claim 3, wherein during the emulsion copolymerization the surface-active comonomer component (c) is initially introduced into the water phase.

5. A method of thickening aqueous systems and aqueous dispersions comprising incorporating into aqueous sytems and aqueous dispersions an amount of a copolymer of claim 1 sufficient to thicken the same.

6. The method of claim 5 wherein said copolymers are mixed in their unneutralized form capable of salt formation as solutions or dispersions in the required amount with the aqueous system to be thickened or with the dispersion to be thickened, and then partially or completely neutralizing the resulting mixture by addition of bases in the case of anionic copolymers or making it weakly alkaline, or partially or completely neutralizing by addition of acids in the case of cationic copolymers or making it weakly acidic, so that the copolymers are present as water-soluble or colloid-dispersible copolymer salts.

7. The method of claim 5 wherien said copolymer is present in amounts of 0.01 to 5% by weight of copolymer, relative to the aqueous system to be thickened.

8. The method of claim 5 wherein said thickened aqueous system or aqueous dispersion is emulsion paints, gloss emulsion paints, textile printing pastes, paper printing pastes, preparations of biocides, liquid fertilizers, emulsion cleaners, pickling pastes, de-icing agents and cosmetic preparations.

9. The method of claim 5 wherein said thickened aqueous system or aqueous dispersion is a sizing material in the textile industry.

* * * * *

UNITED STATES PATENT AND TRADEMARK OFFICE
CERTIFICATE OF CORRECTION

PATENT NO. : 5,102,936

DATED : April 7, 1992

INVENTOR(S) : HANS-ULLRICH HUTH, KLAUS ZIMMERSCHIED

It is certified that error appears in the above-identified patent and that said Letters Patent is hereby corrected as shown below:

| Col. | Line | | |
|---|---|---|---|
| 13 | 42 | "pl(b)" | should be --b)-- |
| 14 | 22 | "7/2" | should be --7/2-- |
| 15 | 64 | " " " " " " " " " " | |
| 15 | 66&67 | "(CHd 7" | should be --($C_7$-$C_{30}$)-- |

Signed and Sealed this

Twenty-ninth Day of June, 1993

Attest:

MICHAEL K. KIRK

Attesting Officer

Acting Commissioner of Patents and Trademarks